(12) United States Patent
Jönsson et al.

(10) Patent No.: US 8,110,383 B2
(45) Date of Patent: Feb. 7, 2012

(54) FERMENTATION PROCESS STARTING FROM CELLULOSIC BIOMASS AND INVOLVING THE RECIRCULATION OF DETOXIFIED STILLAGE INTO THE PROCESS

(75) Inventors: Leif Jönsson, Umeå (SE); Björn Alriksson, Karlstad (SE)

(73) Assignee: Sekab E-Technology AB, Ornskoldsvik (SE)

( * ) Notice: Subject to any disclaimer, the term of this patent is extended or adjusted under 35 U.S.C. 154(b) by 0 days.

(21) Appl. No.: 13/121,611

(22) PCT Filed: Sep. 30, 2009

(86) PCT No.: PCT/EP2009/062690
§ 371 (c)(1),
(2), (4) Date: May 31, 2011

(87) PCT Pub. No.: WO2010/037780
PCT Pub. Date: Apr. 8, 2010

(65) Prior Publication Data
US 2011/0217746 A1 Sep. 8, 2011

(30) Foreign Application Priority Data
Sep. 30, 2008 (EP) .................................. 08165507

(51) Int. Cl.
C12P 7/06 (2006.01)
C12P 7/04 (2006.01)
(52) U.S. Cl. .................................. 435/161; 435/157
(58) Field of Classification Search .................. 435/157, 435/161
See application file for complete search history.

(56) References Cited
FOREIGN PATENT DOCUMENTS
WO WO 01/60752 A1 8/2001

OTHER PUBLICATIONS

Alriksson et al., "Cellulase Production from Spent Lignocellulose Hydrolysates with Recombinant *Aspergillus niger*", Applied Enviromental Microbiology, vol. 75, pp. 1-40, Feb. 27, 2009, XP008103336.
Friedrich et al., "Use of Fungi for Bioconversion of Distillery Waste", Handbook of Applied Mycology, vol. 4, pp. 963-992, 1992, XP002520107.
Palmqvist et al., "Simultaneous Detoxification and Enzyme Production of Hemicellulose Hydrolysates Obtained after Steam Pretreatment", Enzyme and Microbial Technology, vol. 20, pp. 286-293, 1997, XP007904791.
Rose et al., "Constitutive Expression of the *Trichoderma reesei* β-1,4-Xylanase Gene (xyn2) and the β-1,4-Endoglucanase Gene (egl) in *Aspergillus niger* in Molasses and Defined Glucose Media", Applied Microbiology Biotechnology, vol. 58, No. 4, pp. 461-468, Mar. 1, 2002, XP002487155.
Yang et al., "Production of Acid Protease Using Thin Stillage From a Rice-Spirit Distillery by *Aspergillus niger*", International Food Information Service (IFIS), Database Accession No. 1999-00b0947, 1998, XP002520108.

*Primary Examiner* — Maryam Monshipouri
(74) *Attorney, Agent, or Firm* — Birch, Stewart, Kolasch & Birch, LLP

(57) ABSTRACT

A method for preparing a target chemical derivable from cellulosic biomass, involving detoxification of spent hydrolysate is provided. The method comprises the steps of providing cellulosic biomass, subjecting the cellulosic biomass to aqueous pretreatment, aqueous hydrolysis, and fermentation under conditions in which at least a part of the fermentable sugars are fermented into a primary target chemical, separating the primary target chemical from the fermented hydrolysate to provide a spent hydrolysate comprising inhibitory substances and detoxifying the spent hydrolysate by decreasing the concentration of at least one of the inhibitory substances using a detoxification biocatalyst selected from the group consisting of wild type, mutant and recombinant filamentous fungi and recirculating at least a part of the detoxified spent hydrolysate, optionally after further purification.

16 Claims, 4 Drawing Sheets

FERMENTATION PROCESS STARTING FROM CELLULOSIC BIOMASS AND INVOLVING THE RECIRCULATION OF DETOXIFIED STILLAGE INTO THE PROCESS This application is a 371 of PCT/EP09/62690, filed Sep. 30, 2009, which claims foreign priority to European application No. 08165507.8 filed Sep. 30, 2008.

TECHNICAL FIELD OF THE INVENTION

The present invention relates to a method for preparing a target chemical from cellulosic biomass, to a system for preparing a target chemical from cellulosic biomass and to the use of wild type, mutant or recombinant filamentous fungi for detoxifying spent cellulosic hydrolysate.

BACKGROUND ART

Global warming, petroleum depletion and energy security have been the main driving forces for the development of renewable fuels that can replace the petroleum-derived fuels, such as gasoline and diesel. Ethanol is currently the most commonly used renewable automobile fuel. It is largely produced by fermentation of sugar- or starch-containing feedstocks, such as cane sugar, corn and wheat. However, the supply of these crops is relatively limited, and many of them can be considered as a human food resource. Another disadvantage is that the production of ethanol from most of these raw materials gives a relatively low net energy gain and a low renewable $CO_2$-efficiency, i.e. the amount of fossil $CO_2$ produced throughout the production chain when producing ethanol from these materials is high. Lignocellulose is a more abundant and less expensive raw material with the potential to give a higher net energy gain.

Lignocellulose is primarily composed of cellulose, hemicellulose and lignin. Cellulose is composed of polysaccharide chains of several hundred to over ten thousand linked glucose units, whereas hemicellulose is a polysaccharide composed of xylose, other pentose sugars and various hexose sugars. Cellulose and hemicellulose are tightly associated to lignin, a polyphenolic compound that ties the cellulose and hemicellulose polymers together, thus providing the wood with rigidity and mechanical strength.

In the production of ethanol from lignocellulosic materials, various pretreatment and hydrolysis steps are used to degrade the cellulose and hemicellulose polysaccharides in the lignocellulose to monosaccharides. Microorganisms can then be used to ferment the monosaccharides to ethanol. The yeast *Saccharomyces cerevisiae*, which metabolizes hexose sugars, is one of the most suitable microorganisms for ethanol production and is favoured in industrial processes.

However, as the lignocellulose is degraded, a broad range of substances are released, some of which can be toxic and inhibit microorganisms, e.g. the yeast *S. cerevisiae*, which are used for ethanol fermentation. Further, the inhibitory substances may also be rate limiting for enzymes used in the hydrolysis of the lignocellulosic biomass. The nature and amount of inhibitory substances depend on the type of lignocellulosic raw material and the pretreatment and hydrolysis processes used. Examples of inhibitory substances include aliphatic acids such as acetic acid, which is released as the hemicellulose fraction is degraded, furan aldehydes, furfural and different phenolic compounds. The presence of such inhibitory substances thus results in lower ethanol yield and productivity.

Furthermore, it is desirable to recycle the process water in an ethanol production plant, for example to minimize the addition of fresh water and consequently minimize the production costs and/or to reduce the environmental impact. However, recycling of the process water can lead to an accumulation and build-up in the concentration of inhibitory substances, which is an obstacle for reusing the process water. There are several methods to avoid inhibitor-related problems, but they are often associated with additional process cost or other problems.

WO 01/60752 discloses a process for treating the wastewater effluent to decrease the levels of inhibitory substances when producing ethanol from lignocellulose. However, WO 01/6752 involves complex anaerobic digestion with methane producing microorganisms before reusing the wastewater effluent.

Palmqvist et al (*Enzyme and Microbial Technology.* 1997, 20, p. 286-293) discloses a method for simultaneous enzyme production and detoxification of hemicellulose hydrolysates. However, the method involves detoxification with *Trichoderma reesei* prior to ethanol fermentation, meaning that hexoses are consumed by *T. reesei* prior to the fermentation instead of being used for ethanol production, and recirculation of the process water starts prior to fermentation, meaning that only a small portion of the total process water is recirculated.

To summarize, the prior art fails to provide an attractive method for producing ethanol that is simple and allows for detoxification and recirculation of the process water.

SUMMARY OF THE INVENTION

It is an aim of some aspects of the present disclosure to provide for reduction of the amounts of fresh water needed for the production of a target chemical, such as ethanol, and/or the amounts of waste water formed in such production.

Further, it is an aim of some aspects of the present disclosure is to provide a system for production of a target chemical, such as ethanol, from cellulosic biomass.

Still further, it is an aim of some aspects of the present disclosure is to provide for reduction of toxic and/or inhibiting by-products from process water during the production of the target chemical.

The present invention is defined by the appending claims. One aspect of the invention provides a method for preparing at least one target chemical derivable from cellulosic biomass involving detoxification of spent hydrolysate, comprising the steps of:
a) providing cellulosic biomass;
b) subjecting the cellulosic biomass to at least one aqueous pretreatment fluid to provide pretreated cellulosic biomass;
c) subjecting the pretreated cellulosic biomass to at least one aqueous hydrolysing liquid, optionally comprising saccharification enzymes, under conditions in which at least a part of the pretreated cellulosic biomass is hydrolysed to a cellulosic hydrolysate, said cellulosic hydrolysate comprising fermentable sugars and inhibitory substances;
d) subjecting the fermentable sugars to fermentation in an aqueous liquid fermentation utilizing at least one fermentation biocatalyst under conditions in which at least a part of the fermentable sugars are fermented into a primary target chemical;
e) separating the primary target chemical from the fermented hydrolysate to provide a spent hydrolysate comprising inhibitory substances;

f) detoxifying the spent hydrolysate by decreasing the concentration of at least one of the inhibitory substances using a detoxification biocatalyst selected from the group consisting of wild type, mutant and recombinant filamentous fungi, to provide a detoxified spent hydrolysate;

g) recirculating at least a part of the detoxified spent hydrolysate, optionally after further purification, as a part of aqueous liquid(s) provided in at least one of steps b), c) and d).

In an embodiment, the fermentation biocatalyst of step d) is yeast, and the primary target chemical of step d) is ethanol.

In an embodiment, the fermentation biocatalyst is wild type, mutant or recombinant *Saccaromyces cerevisiae.*

In an embodiment, the cellulosic biomass of step a) is selected from wood material, municipal paper waste, agricultural residues, such as bagasse, and energy crops.

In an embodiment, the aqueous pretreatment liquid of step b) has a pH of below 5.

In an embodiment, the primary target chemical is separated from the fermented hydrolysate in step e) by means of distillation.

In an embodiment, the inhibitory substances comprise furan aldehydes, such as furfural and/or HMF, aliphatic acids and/or phenolic compounds.

In an embodiment, the detoxification biocatalyst of step f) is fungus selected from wild type, mutant or recombinant *Aspergillus, Trichoderma, Rhizopus, Mucor*, or a combination thereof.

In an embodiment, the detoxification biocatalyst is wild type, mutant or recombinant *Aspergillus niger.*

In an embodiment, the detoxification biocatalyst produces enzymes during the detoxification in step f).

In an embodiment, the enzymes are saccharification enzymes.

In an embodiment, the saccharification enzymes obtained in step f) are added in the aqueous hydrolysing liquid in step c).

An aspect of the invention provides a system for producing at least one target chemical derivable from cellulosic biomass, comprising;
 a) at least one cellulosic biomass pretreatment vessel for pretreating at least a part of provided cellulosic biomass to pretreated cellulosic biomass, connected to
 b) a hydrolysis vessel for hydrolysing at least a part of the pretreated cellulosic biomass to cellulosic hydrolysate, said cellulosic hydrolysate comprising fermentable sugars and inhibitory substances, further connected to
 c) a fermentation vessel comprising a fermentation biocatalyst for fermenting at least a part of the fermentable sugars, providing a fermented hydrolysate comprising the primary target chemical and inhibitory substances, further connected to
 d) a first separation means, for separating the primary target chemical from the fermented hydrolysate and for providing a spent hydrolysate, further connected to
 e) a detoxification vessel, comprising a detoxification biocatalyst selected from the group consisting of wild type, mutant and recombinant filamentous fungi, for detoxifying the spent hydrolysate from at least one inhibitory substance and for providing a detoxified spent hydrolysate, further connected to
 f) recirculation means for recirculating at least a part of the detoxified spent hydrolysate to at least one of the at least one pretreatment vessel of a), the hydrolysis vessel of b) and the fermentation vessel of c), wherein the hydrolysis vessel and the fermentation vessel may be the same vessel or two different vessels.

In an embodiment, the detoxification vessel of e) is connected to the recirculation means f) via second separating means for separating detoxification biocatalyst from at least part of the detoxified spent hydrolysate.

A further aspect of the invention provides the use of wild type, mutant or recombinant filamentous fungi for detoxifying spent cellulosic hydrolysate. An embodiment provides the use of wild type, mutant or recombinant *Aspergillus niger* for detoxifying spent cellulosic hydrolysate.

DETAILED DESCRIPTION OF THE INVENTION

As an aspect of the invention, there is provided a method for preparing at least one target chemical derivable from cellulosic biomass involving detoxification of spent hydrolysate, comprising the steps of:
 a) providing cellulosic biomass;
 b) subjecting the cellulosic biomass to at least one aqueous pretreatment fluid to provide pretreated cellulosic biomass;
 c) subjecting the pretreated cellulosic biomass to at least one aqueous hydrolysing liquid, optionally comprising saccharification enzymes, under conditions in which at least a part of the pretreated cellulosic biomass is hydrolysed to a cellulosic hydrolysate, said cellulosic hydrolysate comprising fermentable sugars and inhibitory substances;
 d) subjecting the fermentable sugars to fermentation in an aqueous liquid utilizing at least one fermentation biocatalyst under conditions in which at least a part of the fermentable sugars are fermented into a primary target chemical;
 e) separating the primary target chemical from the fermented hydrolysate to provide a spent hydrolysate comprising inhibitory substances;
 f) detoxifying the spent hydrolysate by decreasing the concentration of at least one of the inhibitory substances using a detoxification biocatalyst selected from the group consisting of wild type, mutant and recombinant filamentous fungi, to provide a detoxified spent hydrolysate;
 g) recirculating at least a part of the detoxified spent hydrolysate, optionally after further purification, as a part of aqueous liquid(s) provided in at least one of steps b), c) and d).

In the context of the present disclosure, a target chemical derivable from cellulosic biomass refers to a chemical that can be derived or produced from cellulosic biomass by chemical reactions. Examples of target chemicals derivable from cellulose include alcohols, such as ethanol and butanol, acids, alkanes, alkenes, aromatics, aldehydes, ketones, biopolymers, proteins, peptides, amino acids, vitamins, antibiotics and other pharmaceuticals.

Cellulosic biomass refers to biological material made of cellulose. The cellulosic biomass may be lignocellulosic biomass, i.e. biomass that comprises cellulose, hemicellulose and lignin.

The cellulosic biomass may be provided as a grinded form of the cellulosic biomass, such as cellulosic biomass grinded to a size of 1-100 mm, such as 1-80 mm, such as 1-50 mm. Other forms of cellulosic biomass are well-known to the skilled person.

Without being limited thereto, the cellulosic biomass of step a) may be selected from wood material, municipal paper waste, agricultural residues, such as bagasse, and energy crops.

These sources of cellulosic biomass are abundant raw materials with the potential to give a high net energy gain and has a high renewable $CO_2$ efficiency. The wood material may be forestry residues, such as wood chips, sawmill or paper mill discards. The municipal paper waste may be recycled paper or paperboard. Agricultural residues may be corn stover, corn fiber, wheat straw, sugarcane bagasse, beet pulp, rice straw or soybean stover and energy crops may be fast growing trees or woody grasses. Other sources of cellulosic biomass are well-known to the skilled person.

Step b) may be performed by subjecting the cellulosic biomass to at least one aqueous pretreatment fluid under conditions in which at least a part of the cellulosic biomass is hydrolysed. Step b) may, for example, increase the accessibility of cellulose and hemicellulose to saccharification enzymes if such are used for hydrolysis in step c). Step b) may occur in a cellulosic biomass pretreatment vessel. The aqueous pretreatment fluid may be a liquid or a gas or a mixture between a liquid and a gas. Subjecting the cellulosic biomass to at least one aqueous pretreatment fluid may be performed by different techniques known to the skilled man. Thus, step b) may involve one or several pretreatments, such as pretreatment with one aqueous fluid followed by pretreatment with another aqueous fluid. As examples, pretreatment may involve prehydrolysis, impregnation, steaming, steam explosion or any combination thereof. Steaming refers to a process used to drive air out from the cellulosic biomass to facilitate further hydrolysis of the cellulose. Steam explosion refers to a process that combines steam, shearing forces and hydrolysis for rupturing cellulosic fibers. The pretreatment fluid may comprise acid so that the cellulose within the cellulose fibers becomes accessible for subsequent hydrolysis steps. For example, the pH of the pretreatment fluid may be 0.5-5. As a further example, if the pretreatment is impregnation, the pretreatment fluid may be an acid diluted with at least part of the recirculated detoxified spent hydrolysate so that the pretreatment fluid has a pH of 0.5-5, such as 0.5-2. The lower pH interval may be beneficial if a wood-derived cellulosic biomass is used. Also, the pretreatment fluid may for example be applied at a high temperature, such as 50-220° C., preferably 100-220° C. under high pressure, such as a pressure that is higher than atmospheric pressure. Typically, the pretreatment is performed high pressure if the temperature of the pretreatment liquid is 100° C. or higher. The pretreatment fluid may also be an alkaline liquid or an organic liquid.

If lignocellulosic biomass is used, pretreating the lignocellulosic biomass may be performed by using a fluid under conditions so that part of the cellulose and hemicellulose is liberated from lignin.

The aqueous pretreatment fluid of step b) may be a liquid having a pH of below 5, such as below 4, such as below 3, such as below 2. Liquids of low pH, such as acidic solutions, are known to be effective for hydrolysing and dissolving cellulose and hemicellulose, thus allowing good accessibility of the cellulose to further hydrolysis.

As an example, the pretreatment may be impregnation of the cellulosic biomass and in such case the aqueous pretreatment fluid may comprise at least part of the recirculated detoxified spent hydrolysate and an acid. For example, the pH of such aqueous pretreatment fluid may be 0.5-5, such 0.5-2. Alternatively, in an impregnation, the acid may be added as a gas and the aqueous pretreatment fluid may be added as a liquid and comprise at least part of the recirculated detoxified spent hydrolysate.

Subjecting the pretreated cellulosic biomass to an aqueous hydrolysing liquid, optionally comprising saccharification enzymes, under conditions in which at least a part of the pretreated cellulosic biomass is hydrolysed refers to subjecting the pretreated cellulosic biomass to an aqueous hydrolysing liquid, so that a substantial part of the polysaccharides of the cellulosic biomass are depolymerized to free sugars. If lignocellulosic biomass is used, lignin may also be removed from the cellulosic biomass. Preferably, at least 95% of all lignin is separated from the carbohydrates during this step. The free sugars are for example pentoses and hexoses, i.e. monosaccharides having five and six carbon atoms, respectively. This step may occur in a hydrolysis vessel.

The aqueous hydrolysing liquid may comprise enzymes. The enzymes may be saccharification enzymes, i.e. enzymes that can convert or hydrolyse the pretreated cellulosic biomass into free sugars. Such saccharification enzymes may be glycosidases, which hydrolyse polysaccharides. Examples of glycosidases include cellulose-hydrolysing glycosidases, such as cellulases, endoglucanases, exoglucanases, cellbiohydrolases and β-glucosidases, hemicellulose hydrolysing glycosidases, such as xylanases, endoxylanases, exoxylanases, β-xylosidases, arabinoxylanases, mannases galactases, pectinases and glucuronases, and starch hydrolysing glycosidases, such as amylases, α-amylases, β-amylases, glucoamylases, α-glucosidases and isoamylases, or any enzymes in the group of enzymes found in EC 3.2.1.x, such as EC 3.2.1.4, where EC is the Enzyme Commission number.

For example, the saccharification enzyme may be the *Hypocrea jecorina* endoglucanase Cel7B.

Alternatively, the aqueous hydrolysing liquid may comprise at least one mineral acid and/or sulphurous acid, which may be added to the liquid as a gas. Such hydrolysing liquid is suitable for acidic hydrolysis of the biomass. For example, the mineral acid may be sulphuric acid, hydrochloric acid or nitric acid. The acidic hydrolysis may be performed at a certain pH, a certain temperature and certain pressure during a certain time. Acidic hydrolysis of pretreated cellulosic biomass is a well established technique, and it is within the capabilities of the skilled artisan to adjust the pH, i.e. the amount of acid added, temperature, pressure and time to achieve a satisfactory result. For example, the pH of the aqueous hydrolysing liquid comprising at least one mineral acid and/or $SO_2$ may be between 0 and 4.

Subjecting the pretreated cellulosic biomass to an aqueous hydrolysing liquid results in a cellulosic hydrolysate comprising fermentable sugars and inhibitory substances. Fermentable sugars refer to substances such as hexoses and pentoses, which can be converted by living or nonliving ferments.

Inhibitory substances refer to substances that may be rate limiting or inhibitory if present in one or more of the steps in the process for preparing the target chemical. In particular, the inhibitory substances may be substances which are inhibitory to the fermentation of step d), e.g., to yeast. The extent of inhibition caused by the inhibitory substances depends, of course, on their concentrations. For example, the inhibitory substances may be selected from substances which are rate limiting or inhibitory to the fermentation of step d) at a concentration of 100 mM. The person skilled in the art is aware of examples of such inhibitory substances resulting from hydrolysis of cellulose. For example, he may find such examples in Taherzadeh et al. (2000), Larsson et al. (1999) and/or Larsson et al. (2000) referred to below. The inhibitory substances may comprise: furans, such as furan aldehydes, which may be inhibitory at a concentration of 30 mM (or higher) (Taherzadeh et al. 2000 Appl Microbiol Biotechnol 53, 701-708); aliphatic acids, which may be inhibitory at a concentration of 100 mM (or higher) (Larsson et al. 1999 Enzyme Microb Technol 24, 151-159); and/or phenolic compounds, which may be inhibitory at a concentration of 0.1 mM (or higher) (Larsson et al. 2000 Appl Biochem Biotechnol 84-86, 617-632). These compounds are known to inhibit the yeast *S. cerevisiae*, which results in lower ethanol yield and productivity. Examples of furan aldehydes may be furfural or 5-hydroxymethylfurfural (HMF), and the aliphatic acid may be acetic acid. Subjecting the fermentable sugars to fermentation in an aqueous liquid utilizing at least one fermentation biocatalyst under conditions in which at least a part of the cellulosic hydrolysate is fermented into a primary target chemical refers to using at least one fermentation biocatalyst for fermenting the free sugars into the primary target chemical of the process. Thus, the fermentation of step d) may be performed by one or several types of fermentation biocatalysts. A fermentation biocatalyst refers to a substance or microorganism that causes free sugars to break down into the primary target chemical, e.g. due to anaerobic breakdown. This step may occur in a fermentation vessel.

The aqueous fermentation may comprise an aqueous fermentation liquid. The aqueous fermentation liquid may comprise the at least one fermentation biocatalyst. Further, the at least one fermentation biocatalyst may be immobilized.

The fermentation biocatalyst of step d) may be yeast, and the primary target chemical of step d) may be ethanol.

In the context of the present disclosure, yeast refers to single-celled members of the fungal families. Yeasts are known to be able to ferment sugars into more simple molecules. Yeasts from *Saccharomyces, Pichia* and *Candida* may be used as the fermentation biocatalyst. Ethanol is an example of a chemical that is derivable from cellulose and can be produced by yeast through fermentation. Other examples of target chemicals derivable from cellulose include other alcohols, such as butanol, acids, alkanes, alkenes, aromatics, aldehydes, ketones, biopolymers, proteins, peptides, amino acids, vitamins, antibiotics and other pharmaceuticals.

The fermentation biocatalyst may be wild type, mutant or recombinant *Saccaromyces cerevisiae*. *S. cerevisiae* is one of the most suitable microorganisms for ethanol production from hexose sugars and is favored in industrial processes.

Alternatively, or as a complement, the fermentation biocatalyst may be separated from the fermented hydrolysate after the fermentation of step d).

Separating the primary target chemical, and, if applicable, the fermentation biocatalyst from the fermented hydrolysate refers to removing the primary target chemical and, if applicable, the fermentation biocatalyst from the fermented hydrolysate. Preferably, at least 95% of the target chemical and, if applicable, the fermentation biocatalyst, are removed in such separation. This step may occur in a first separation means. The fermented hydrolysate may comprise the primary target chemical, unfermented sugars and inhibitory substances.

The primary target chemical may be separated from the fermented hydrolysate in step e) by means of distillation. Distillation refers to separation of a liquid mixture into its components on the basis of differences in boiling points. As an example, if the target chemical is ethanol, distillation is a preferred method for separating ethanol from the fermented hydrolysate due to the lower boiling point of ethanol compared to the other substances comprised in the fermented hydrolysate. The resulting hydrolysate may thus be a spent hydrolysate comprising the inhibitory substances as described above. As an example, the spent hydrolysate may be a stillage, i.e. the spent effluent after distillation.

Detoxifying the spent hydrolysate from at least one of the inhibitory substances refers to subjecting the spent hydrolysate to a treatment so as to reduce the levels, or concentrations, of the at least one inhibitory substance. For example, the concentration of the at least one inhibitory substance may be reduced by at least 50%. Also, the level, or concentration of the at least one of inhibitory substance is preferably reduced such that, in the above-mentioned method for preparing at least one target chemical derivable from cellulosic biomass involving detoxification of spent hydrolysate and recirculation of the detoxified hydrolysate, the at least one inhibitory substances are not inhibitory or rate limiting in step c) or d) of the method. "Not inhibitory or rate limiting" in a step may be lowering the yield of the step by 1% or less, such as 0.5% or less, such as 0.1% or less.

However, the main purpose of the detoxification is to prevent accumulation in the method (which comprises recirculation). Consequently, the detoxification may be reducing the level, or concentration, of the at least one inhibitory substance so as to prevent accumulation of the substance.

This detoxification step may occur in a detoxification vessel. The detoxification biocatalyst is selected from the group consisting of wild type, mutant and recombinant filamentous fungi. Filamentous fungi refer to fungi that live as multicellular filaments (hyphae), which form a mycelium. Wild type filamentous fungi refers to the original parent strain of the filamentous fungi, i.e. filamentous fungi that are found naturally, or in the wild, whereas mutant filamentous fungi refers to filamentous fungi that differ from the wild type filamentous fungi by one or more functional mutations, i.e. having one or more permanent changes in the genetic material affecting the phenotype. Recombinant filamentous fungi refer to filamentous fungi that contain DNA from one or more additional sources, e.g. having an addition of relevant DNA, such as the plasmid of a bacteria, into the genome. The provided mutant or recombinant fungi possess at least 10%, preferably at least 50%, such as at least 90% of the ability to consume the inhibitory substances of the corresponding wild type fungi. Also, the provided mutant or recombinant fungi may have a higher ability to consume the inhibitory substances compared to the wild type. Example of such inhibitory substances are mentioned above. The ability to consume the inhibitory substances may for example be performed according to Examples, section Chemical Analyses, below. The skilled person understands how to compare such ability of a wild type fungi with that of a mutant or recombinant.

The inventors have noted that filamentous fungi represent a group of organisms that is typically characterized by an ability to grow on simple and inexpensive substrates, a high metabolic versatility, a saprophytic life style connected with an ability to degrade a variety of different organic substances, suitability for use in aerobic processes, and a well developed capacity to secrete metabolites and proteins. Such features, which are commonly shared by different species of filamentous fungi, make them into a group of organisms suitable to use in the same way as demonstrated with respect to a fungus of the genus *Aspergillus* that can be regarded as a model organism among the filamentous fungi (Baker S E (2006) Medical Mycology 44, S17-S21).

The detoxification biocatalyst of step f) may be a filamentous fungi selected from wild type, mutant or recombinant *Aspergillus, Trichoderma, Rhizopus, Mucor*, or a combination thereof. In the present disclosure, *Aspergillus* has shown to have outstanding detoxification capabilities, and all inhibitors tested served as an excellent growth medium for *Aspergillus*. *Trichoderma, Rhizopus, Mucor* are filamentous fungi sharing relevant characteristics with *Aspergillus*. For example, the inventors have noted that *Hypocrea jecorina* (frequently referred to as *Tricoderma reesei*) is growing well in spent stillage from a distillation of a fermentation broth from a fermentation of lignocellulose hydrolyzate. The fungus has also been found to produce enzyme activity (xylanase activity) when it was growing. Together, this indicates detoxification activity. Further, it shows that *Hypocrea jecorina* may be employed in the embodiments also involving enzyme production discussed below. Other filamentous fungi that can be used are *Trametes, Sclerotium, Aureobasidium, Schizophyllum, Acremonium, Tolypocladium, Claviceps, Monascus, Taxomyces, Fusarium* and *Agaricus*. Combinations of filamentous fungi from different families may also be used, such as filamentous fungi from both *Aspergillus* and *Trichoderma*.

The filamentous fungi may be wild type, mutant or recombinant *Aspergillus niger*. In the present disclosure, *Aspergillus niger* has shown to have outstanding detoxification capabilities, and all inhibitors tested served as an excellent growth medium for *A. niger*. Other useful *Aspergillus* species may be wild type, mutant or recombinant *A. caesiellus, A. candidus, A. carneus, A. clavatus, A. deflectus, A. flavus, A. fumigatus, A. glaucus, A. nidulans, A. ochraceus, A. oryzae, A. parasiticus, A. penicilloides, A. restrictus, A. sojae, A. sydowi, A. tamari, A. terreus, A. ustus* or *A. versicolor*.

The *Aspergillus niger* may be a strain expressing the *Hypocrea jecorina* endoglucanase Cel7B. In the present disclosure, a strain of *Aspergillus niger* expressing the *Hypocrea jecorina* endoglucanase Cel7B has shown to have detoxification capabilities, and all inhibitors tested served as an excellent growth medium for this strain of *A. niger*. However, this strain is only one example of many which may be employed in the context of the present disclosure.

The detoxification biocatalyst may produce enzymes during the detoxification in step f). The enzyme production may be endogenous or may be achieved by inserting the DNA of any enzyme into the genome of the detoxification biocatalyst, i.e. using a recombinant detoxification biocatalyst. Suitable enzymes may be any industrial important enzymes, such as xylanases, amylases, ligninases, cellulases, cellobiases or proteases.

The enzymes may be saccharification enzymes. Saccharification enzymes are referred to as above, i.e. enzymes that can convert or hydrolyse the pretreated cellulosic biomass into free sugars. A saccharification enzyme may be the *Hypocrea jecorina* endoglucanase. In the present disclosure, a detoxification biocatalyst producing saccharification enzymes exhibited outstanding detoxification capabilities. Moreover, all inhibitors tested served as excellent growth media for the detoxification biocatalyst producing saccharification enzymes. The enzymes produced can be purified and utilized in different applications.

The saccharification enzymes obtained in step f) may be added in the aqueous hydrolysing liquid in step c). Recirculation refers to using at least part of the saccharification enzymes obtained in step f), as a part of the aqueous hydrolysing liquid comprising saccharification enzymes in step c). This is schematically illustrated in FIG. 2. Recirculation of produced saccharification enzymes is an excellent way to minimize the use of external enzymes when hydrolysing cellulose and hemicellulose before fermentation.

The detoxification biocatalyst may be immobilized.

Alternatively, or as a complement, the detoxification biocatalyst may be separated from the detoxified spent hydrolysate, which refers to removing detoxification biocatalyst from the hydrolysate. Preferably, at least 95% w/w of the detoxification biocatalyst is removed in such separation. This step may occur in a second separation means. As an example, various filtering techniques may be used. The separated detoxification biocatalyst may be further used for various purposes. As an example, the separated detoxification biocatalyst can be utilized as a protein source in various products, such as a protein source in cattle feed. Also, the detoxification biocatalyst may be separated by means of sedimentation of centrifugation.

Recirculating at least a part of the detoxified spent hydrolysate, optionally after further purification, as a part of the aqueous liquid(s) provided in at least one of steps b), c) or d) refers to reusing at least part of the detoxified spent hydrolysate obtained in step f) as a part of the aqueous pretreatment liquid of step b), the aqueous hydrolysing liquid of step c) or the aqueous fermentation liquid of step d). This step may occur in recirculation means. The further purification refers to further means for decreasing the levels or concentrations of the inhibitory substances of the detoxified spent hydrolysate. Such further purification may be different filtering and/or adsorption steps. The detoxified spent hydrolysate may be recirculated as a part of the above-mentioned aqueous liquids and may be mixed with fresh water before being recirculated.

The invention is based on the insight that using filamentous fungi for detoxification of the spent hydrolysate after fermentation to provide the target chemical leads to a surprisingly low level of inhibitory substances, so that the detoxified hydrolysate can be recirculated into any part of the process. Filamentous fungi have thus been found to utilize a broad range of compounds as nutrients and compounds that inhibit saccharification enzymes and the fermentation biocatalyst, as seen in Examples 1 to 3. Hence, the use of filamentous fungi removes inhibitory cellulose-derived or lignocellulose-derived substances and thus facilitates recycling of process water. Moreover, detoxification of the spent hydrolysate, i.e. the hydrolysate obtained after separating the primary target chemical from the fermented hydrolysate, allows for recirculation of a substantial part of the water used in the method for preparing the target chemical. Furthermore, the use of filamentous fungi minimizes the need for fresh water in the production of the target chemical derivable from cellulosic biomass. Moreover, the disclosed method advantageously utilizes the efficient aerobic respiration of the filamentous fungi for detoxification and thus does not require the less efficient anaerobic conditions.

The disclosed preparation method is illustrated in FIG. 1 and FIG. 2, and the detoxification using filamentous fungi is exemplified in Examples 1 to 5, which illustrate the efficiency and advantages of the disclosed invention In an embodiment, there is provided a method for preparing at least one target chemical derivable from lignocellulosic biomass, comprising the steps of:
  a) providing lignocellulosic biomass;
  b) subjecting the lignocellulosic biomass to an aqueous pretreatment liquid under conditions in which at least a part of the lignocellulosic biomass is hydrolysed, to provide pretreated lignocellulosic biomass;
  c) subjecting the pretreated lignocellulosic biomass to an aqueous hydrolysing liquid, optionally comprising saccharification enzymes, under conditions in which at least a part of the pretreated lignocellulosic biomass is delignified and further hydrolysed to provide lignin and a lignocellulosic hydrolysate, said lignocellulosic hydrolysate comprising fermentable sugars and inhibitory substances;

d) subjecting the lignocellulosic hydrolysate to an aqueous fermentation liquid comprising a fermentation biocatalyst under conditions in which at least a part of the lignocellulosic hydrolysate is fermented into a primary target chemical, to provide a fermented hydrolysate comprising the primary target chemical, inhibitory substances and the fermentation biocatalyst;

e) separating the fermentation biocatalyst and the primary target chemical from the fermented hydrolysate to provide a spent hydrolysate comprising inhibitory substances;

f) detoxifying the spent hydrolysate from at least one of the inhibitory substances using a detoxification biocatalyst selected from the group consisting of wild type, mutant and recombinant filamentous fungi, to provide a detoxified hydrolysate;

g) separating the detoxification biocatalyst from the detoxified hydrolysate to provide purified process water; and h) recirculating at least a part of the purified process water as a part of the aqueous liquid(s) in at least one of steps b), c) and d).

In a preferred embodiment, there is provided a method for preparing ethanol derivable from lignocellulosic wood material involving detoxification of spent hydrolysate, comprising the steps of:

a) providing lignocellulosic wood material grinded to 1-50 mm;

b) subjecting the lignocellulosic wood material to an aqueous pretreatment liquid of pH 1-5 at a temperature of 100-220° C.;

c) subjecting the pretreated wood material to an aqueous hydrolysing liquid comprising saccharification enzymes, such as cellulases, at a temperature so that the pretreated lignocellulosic is further hydrolysed, to provide lignin and a lignocellulosic hydrolysate, which comprise free hexoses, pentoses, and inhibitory substances, such as furfural, furan aldehydes, aliphatic acids and phenolic compounds;

d) subjecting the lignocellulosic hydrolysate to an aqueous fermentation liquid comprising a yeast, such as *Saccharomyces cerevisiae*, under conditions in which at least a part of the hexoses and pentoses are fermented into ethanol;

e) separating the yeast from the fermented hydrolysate, e.g. by filtering, and using distillation to separate and the ethanol from the fermented hydrolysate, to provide a spent hydrolysate;

f) detoxifying the spent hydrolysate from at least one of the inhibitory substances, such as furfural, furan aldehydes, aliphatic acids and phenolic compounds, using wild type, mutant or recombinant *Aspergillus niger*, to provide a detoxified hydrolysate;

g) separating *Aspergillus niger* from the detoxified hydrolysate to provide purified process water; and h) recirculating at least a part of the purified process water as a part of the aqueous liquid(s) in at least one of steps b), c) and d).

As an aspect of the invention, there is provided a system for producing at least one target chemical derivable from cellulosic biomass, comprising;

a) at least one cellulosic biomass pretreatment vessel for pretreating at least a part of provided cellulosic biomass to pretreated cellulosic biomass, connected to b) a hydrolysis vessel for hydrolysing at least a part of the pretreated cellulosic biomass to cellulosic hydrolysate, said cellulosic hydrolysate comprising fermentable sugars and inhibitory substances, further connected to c) a fermentation vessel comprising a fermentation biocatalyst for fermenting at least a part of the fermentable sugars, providing a fermented hydrolysate comprising the primary target chemical and inhibitory substances, further connected to d) a first separation means, for separating the primary target chemical from the fermented hydrolysate and for providing a spent hydrolysate, further connected to e) a detoxification vessel, comprising a detoxification biocatalyst selected from the group consisting of wild type, mutant and recombinant filamentous fungi, for detoxifying the spent hydrolysate from at least one inhibitory substance and for providing a detoxified spent hydrolysate, further connected to f) recirculation means for recirculating at least a part of the detoxified spent hydrolysate to at least one of the at least one pretreatment vessel of a), the hydrolysis vessel of b) and the fermentation vessel of c), wherein the hydrolysis vessel and the fermentation vessel may be the same vessel or two different vessels.

The activities of pretreating at least a part of provided cellulosic biomass in a cellulosic biomass pretreatment vessel, hydrolysing at least a part of the pretreated cellulosic biomass in a hydrolysis vessel, fermenting at least a part of the fermentable sugars in a fermentation vessel, separating the primary target chemical in a first separation means, detoxifying the spent hydrolysate in a detoxification vessel, recirculating at least a part of the detoxified spent hydrolysate in recirculation means may be performed as described in the disclosure herein above.

The detoxification vessel of e) may be connected to the recirculation means f) via second separating means for separating detoxification biocatalyst from at least part of the detoxified spent hydrolysate.

The activity of separating the detoxification biocatalyst from at least part of the detoxified spent hydrolysate may be performed as described in the disclosure herein above.

As an aspect of the invention, there is provided the use of wild type, mutant or recombinant filamentous fungi for detoxifying spent lignocellulosic hydrolysate.

In most cases, spent lignocellulosic hydrolyzate refers to the stillage resulting from the distillation of the fermentation broth resulting from the fermentation of hydrolyzed lignocellulose. The chemical composition of such stillage differs from the chemical composition of stillage resulting from distillation of the fermentation broth resulting from the fermentation of traditional sugar-containing solutions, such as the sugars-containing solutions derived from starch (e.g. rice or wheat), sugar beets or cane sugar. The difference is at least partly due to substances that are formed/released during the hydrolysis of the lignocellulose. Examples of substances that may be formed during the hydrolysis of lignocellulose are furans, aliphatic acids and phenolic compounds, which are identified as inhibitory substances in the present disclosure.

The spent lignocellulosic hydrolyzate or stillage of the present aspect is thus different from stillages arising in a rice spirit distillery or another production of alcoholic beverages.

Wild type, mutant or recombinant filamentous fungi is referred to as described herein above. The use of wild type, mutant or recombinant filamentous fungi removes a surprisingly high amount of inhibitory substances, and allows for recirculation of the detoxified spent hydrolysate. Further, the use of wild type, mutant or recombinant filamentous fungi minimizes the use of fresh water needed when preparing target chemicals from cellulosic biomass.

The filamentous fungi may be wild type, mutant or recombinant *Aspergillus niger*. In the present disclosure, the use of *Aspergillus niger* has shown to remove a surprisingly high amount of inhibitory substances, and all inhibitors tested served as an excellent growth medium for *A. niger*. Other members of *Aspergillus* may be used, such as those mentioned in the disclosure herein above.

EXAMPLES

Figure 1:
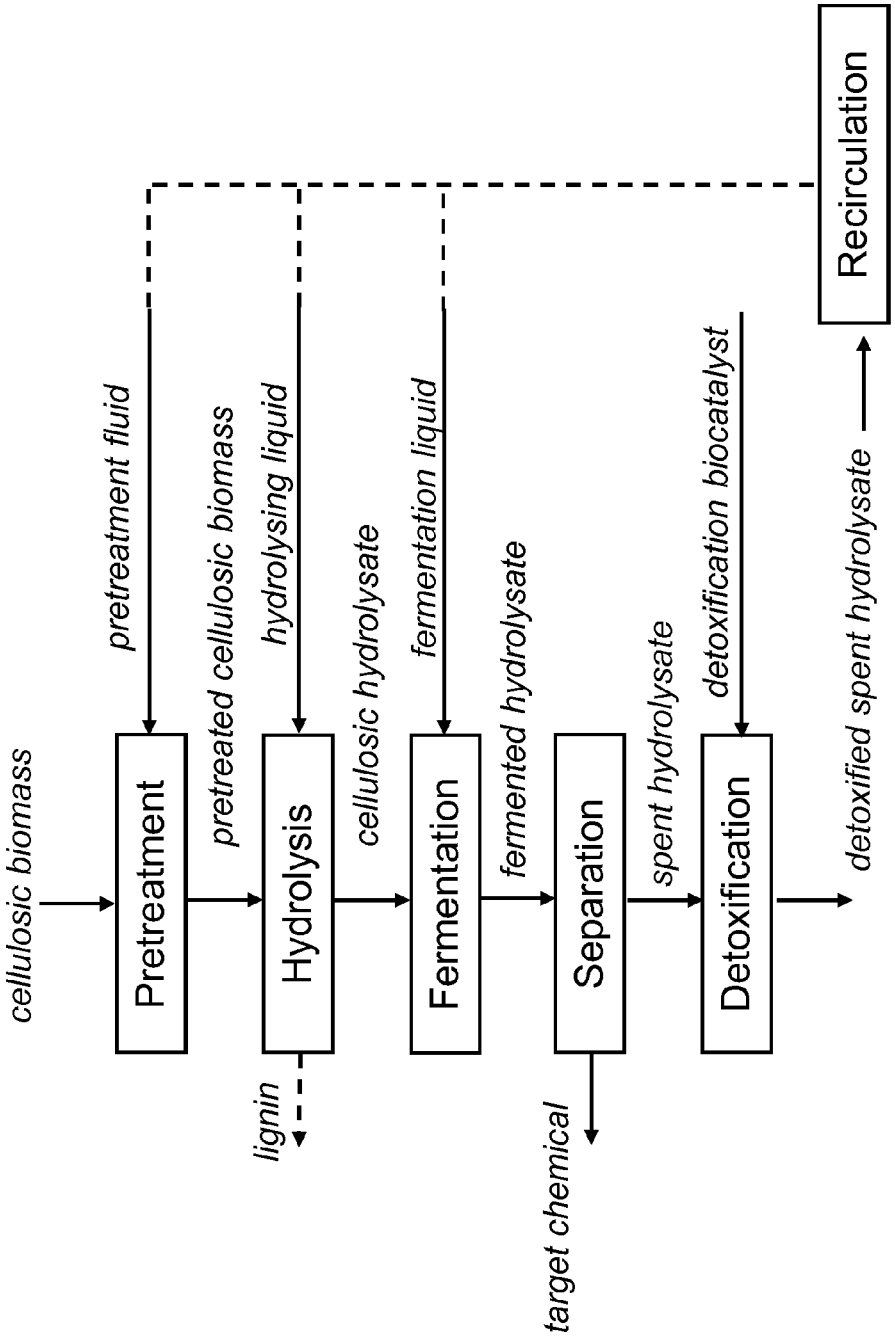
FIG. 1 shows a method for producing a target chemical from cellulosic biomass according to the present disclosure.

The following non-limiting examples will further illustrate the present invention.

Example 1

Detoxification of Spent Bagasse Hydrolysate Using *Aspergillus niger*

Raw Material

Sugarcane bagasse was air-dried to a dry-matter content of 96% and milled to pass a 2 mm screen.

Pretreatment

3×180 g of dried and milled raw material was mixed with 3×1800 g of diluted sulfuric acid in three separate stainless steel cylinders, each with a total volume of 2.5 L. The final concentration of sulfuric acid in the slurry was 2%. The cylinders were attached to a rotor in a polyethylene glycol heating bath controlled by a control unit (Jaako Pöyry AB, Karlstad, Sweden). The pretreatment was performed at 122° C. during 60 min. Directly after the pretreatment was finished, the cylinders were rapidly cooled to room temperature in a water bath. The solids and the liquid of the pretreated slurry were separated by vacuum filtration. The solids were washed with 3×5 L of deionized $H_2O$ and dried in a heating cabinet at 70° C. for 72 h. The liquid fraction, hereafter referred to as bagasse prehydrolysate, was collected and stored at 4° C.

Hydrolysis

Pretreated solid material (80 g dry weight, DW) was mixed with 800 g of bagasse prehydrolysate in a 2000 mL Erlenmeyer glass flask closed with cotton plugs (experiment was done in quadruplet). The pH of the slurries was adjusted to 4.8 with NaOH. Commercially available preparations of cellulase and cellobiase (Celluclast 1.5 L, with a supplier-stated activity of 700 endoglucanase units (EGU)/g (Sigma-Aldrich, Steinheim, Germany) and Novozyme 188, with a stated activity of 250 cellobiase units (CBU)/g (Sigma-Aldrich)) were added to the slurry at a loading of 319 EGU/g of solids (DW) and 23 CBU/g of solids (DW), respectively. The slurries were incubated with shaking (Incubator Shaker model G25, New Brunswick Scientific, Edison, N.J., USA) at 50° C. and 150 rpm for 72 h. The pH of the slurries was measured and readjusted to 4.8 with NaOH every ten hours. During the hydrolysis, the amount of released glucose in the slurries was monitored by measurements with a glucometer (Glucometer Elite XL, Bayer AG, Leverkusen, Germany) every ten hours. After the hydrolysis, the slurries were filtered. The pH of the liquid fraction, hereafter referred to as bagasse hydrolysate, was adjusted to pH 2.0 with HCl and it was then stored at 4° C. to prevent microbial growth during storage.

Fermentation with *S. cerevisiae*

Prior to fermentation, the pH of the bagasse hydrolysates was adjusted to 5.5 with NaOH. The hydrolysates were also supplemented with a nutrient solution giving a final concentration of 0.5 g/L $(NH_4)_2HPO_4$, 0.025 g/L $MgSO_4.7H_2O$, 1.38 g/L $NaH_2PO_4.H_2O$, and 1 g/L yeast extract. The fermentations of the bagasse hydrolysates were carried out in 15 parallel 50-mL glass flasks equipped with magnets for stirring and sealed with rubber plugs pierced by cannulas for $CO_2$ removal. The flasks were inoculated with baker's yeast (*S. cerevisiae*) (Jästbolaget AB, Rotebro, Sweden). The flasks with bagasse hydrolysate were given an inoculum yielding a cell mass concentration of 1 g/L (DW). The flasks were incubated at 30° C. for 5 h in a water bath with magnetic stirring (IKA-Werke, Staufen, Germany). The glucose levels during the course of fermentation were monitored by continuous measurements with a glucometer.

Distillation

After the fermentation, the yeast cells were removed from the fermented hydrolysates by centrifugation (Sorvall RC26 Plus, Dupont, Newtown, Conn., USA) at 1 500 g and 4° C. for 6 min. The pH of the fermented hydrolysate liquids was adjusted to 7.0 with NaOH to prevent possible sugar degradation during the distillation. The fermented hydrolysate liquids were transferred to round-bottom flasks and a few drops of antifoam added to avoid excessive bubble formation during distillation. Standard distillation glass ware was used for the distillation setup and a polyethylene glycol heating bath was used as heat source. The distillation was pursued until all ethanol was separated from the fermented hydrolysate liquids. The non-ethanol fractions remaining in the round-bottom flasks, hereafter called spent bagasse hydrolysate (SBH), were collected and stored at 4° C. until further use.

*A. niger* Recombinant Strains

A recombinant *A. niger* D15 transformant expressing the *H. jecorina* Cel7B gene was used (strain was designated *A. niger* D15[egl]). The expression of the Cel7B gene was under transcriptional control of the constitutive gpd promoter from *A. niger* and the glaA terminator from *Aspergillus awamori*. A transformant with the same promoter and terminator integrated in the chromosome but without the Cel7B gene was used as a negative control (strain was designated *A. niger* D15[pGT]). The construction of the two recombinant strains is described in Rose and van Zyl, 2002 (Rose, S. H. and van Zyl, W. H, *Appl. Microbiol. Biotechnol.* 2002, 58, p. 461-468)

Detoxification Experiment with *A. niger* Grown on Spent Bagasse Hydrolysate

Four 100-mL Erlenmeyer flasks (named A-D) were filled with 48 mL of SBH, 1 mL of nutrient solution (25 g/L $(NH_4)_2HPO_4$, 1.25 g/L $MgSO_4.7H_2O$, 69 g/L $NaH_2PO_4.H_2O$, and 50 g/L yeast extract), 0.05 mL of trace element solution (0.22 g/L $ZnSO_4.7H_2O$, 0.11 g/L $H_3BO_3$, 0.05 g/L $MnCl_2.4H_2O$, 0.05 g/L $FeSO_4.7H_2O$, 0.017 g/L $CoCl_2.6H_2O$, 0.016 g/L $CuSO_4.5H_2O$, 0.015 g/L $Na_2MoO_4.2H_2O$, and 0.5 g/L EDTA) and closed with cotton plugs. The flasks A and B were inoculated with 0.95 mL *A. niger* D15[egl] spores (final spore concentration was $1 \times 10^6$ spores/mL medium). The flasks C and D were inoculated with *A. niger* D15[pGT] spores at an equal concentration. For comparison, four 100-mL Erlenmeyer flasks (named E-H) closed with cotton plugs were filled with 49.05 mL of standard medium (5 g/L yeast extract, 0.4 g/L $MgSO_4.7H_2O$, 10 g/L glucose, 2 g/L casamino acids, 0.5 g/L KCl, 1.5 g/L $KH_2PO_4$, 6 g/L $NaNO_3$, and 1 mL/L of the trace element solution). The flasks E and F were inoculated with 0.95 mL *A. niger* D15[egl] spores and the G and H flasks were inoculated with 0.95 mL *A. niger* D15[pGT] spores (final spore concentration was $1 \times 10^6$ spores/mL medium). The flasks were incubated for eleven days in an incubator with shaking (Incubator shaker model G25, New Brunswick Scientific) at 30° C. and 150 rpm. The endoglucanase activity was monitored during the fermentation experiment and the biomass production was measured at the end of the experiment (see description below).

Biomass Measurement

To determine the dry weight of the *A. niger* biomass, pieces of Miracloth (Calbiochem, EMD Biosciences, La Jolla, Calif., USA) were dried in a microwave oven for 15 min and were thereafter placed in an exsiccator. After 2 h, the Miracloth pieces were taken out of the desiccator and pre-weighed on an analytical scale. The *A. niger* culture suspension volumes from the fermentation experiments were measured and the culture suspensions were then filtered through dried Miracloth under suction. Every piece of Miracloth with biomass was washed with 50 mL of $dH_2O$, dried as previously described, and then weighed.

Enzyme Activity Assay and SDS-PAGE Analysis

The endoglucanase activity was monitored by using a method based on dinitrosalicylic acid as described by Bailey et al., 1992 (Bailey, M. J. et al., *J. Biotechnol.* 1992, 23, p. 257-270.) The buffer used for the assay was citrate (0.05 M, pH 5.5), the substrate was carboxymethyl cellulose (Fluka ultra-low viscosity, Sigma-Aldrich) (1% in citrate buffer 0.05 M, pH 5.5) and the assay was carried out at 50° C. The enzyme activity is given in nkat/mL (nmol produced reducing sugars/mL/s).

Supernatants from the fermentation experiment were diluted four times with $dH_2O$ and loaded onto 10% SDS-PAGE gels to determine the extracellular protein profile as well as the size of the Cel7B protein. Subsequent to electrophoresis, the gel was stained with Sypro Red gel stain (Molecular Probes, Eugene, Oreg., USA) according to Steinberg et al., 1996 (Steinberg, T. H. et al., *Anal. Biochem.* 1996, 239, p. 238-245.). The analysis of the gel was performed with a gel imager (ImageQuant 400, GE Healthcare, Piscataway, N.J., USA). In addition, the Cel7B protein concentration was measured by running a concentration gradient of bovine serum albumin as standard protein (Pierce, Rockford, Ill., USA) as well as the Cel7B supernatants on an SDS-PAGE gel and compare the intensity of the Sypro Red-stained bands using the software ImageJ (rsb.info.nih.qov/ij/). The Cel7B protein concentration was calculated as the mean value of two supernatants from separate cultivation flasks that have been analyzed as four replicates (i.e. on four separate gels). The Sypro Red dye exhibits low variability in the staining of different types of proteins due to its interaction with the dodecyl sulfate coat around the protein in the SDS-PAGE gel (Steinberg, T. H., et al., *Anal. Biochem.* 1996 A_239, p. 223-237). The reported specific activities are based on Cel7B protein measurements. The Cel7B protein measurements were made on samples taken at a fixed time for all samples in one fermentation experiment. The time of measurements was set at the time when the single highest endoglucanase activity was noted during each fermentation experiment.

Chemical Analyses

The content of acetic acid was quantified using a Dionex ICS-2000 chromatography system equipped with a conductivity detector. Separation was performed on an IonPac AS 15 (250×4 mm) column with an IonPac AG15 (50×4) pre-column (Dionex). The total concentration of phenolic compounds was determined using the Folin-Ciocalteu method with vanillin as the standard. The concentrations of furfural and HMF were determined by HPLC. An XTerra MS $C_{18}$ column (5 μm, 2.1×150 mm) (Waters, Milford, Mass., USA) was used in a Shimadzu VP series system (Shimadzu, Kyoto, Japan) with UV detection at 282 nm. Elution was conducted according to the description in Martin et al., 2007 (Martin, C. et al., *Appl. Biochem. Biotechnol.* 2007, 136-140, p. 339-352).

Results

The inhibitor contents in the bagasse prehydrolysate, the bagasse hydrolysate, the hydrolysate after fermentation with *S. cerevisiae*, the SBH and the SBH after fermentation with *A. niger* D15[egl] are shown in Table 1.

It was evident that all the acetic acid, furfural and HMF as well as about 30% of the phenolic compounds was consumed or converted after eleven days of fermentation, shown as SBHAFA in Table 1. The inhibitor concentrations were more or less constant before detoxification, such as after the pretreatment and the fermentation with *S. cerevisiae*, but decreased remarkably after detoxification with *A. niger*. Thus, *A. niger* had a surprisingly high detoxification effect on the spent bagasse hydrolysate, removing almost all inhibitors.

Figure 3:
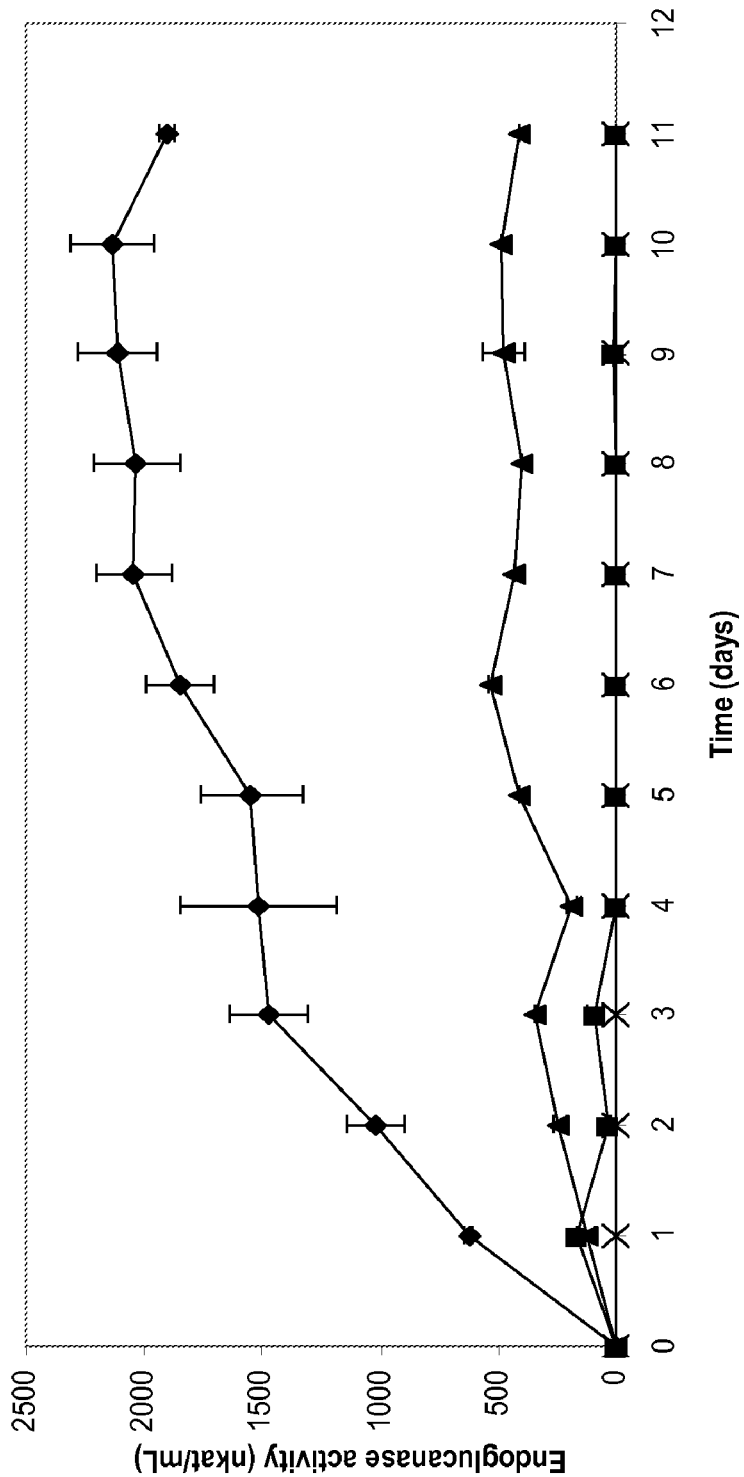
FIG. 3 shows the endoglucanase activity during detoxification of spent bagasse hydrolysate in Example 1. (♦) *A. niger* D15[egl] grown on spent bagasse hydrolysate, (▲) *A. niger* D15[egl] grown on standard medium, (■) *A. niger* D15[pGT] grown on spent bagasse hydrolysate, (x) *A. niger* D15[pGT] grown on standard medium. The endoglucanase activities are calculated as the mean values of activity measurements of two separate cultures. Error bars indicate the standard deviations.

The volumetric activity, Cel7B protein concentration, specific Cel7b activity and biomass production in the fermentation experiment with spent bagasse hydrolysate are presented in Table 2. *A. niger* D15[egl] grown on SBH reached a biomass concentration of 9.8 g/L (DW). As a comparison, when the *A. niger* D15[egl] strain used was grown on standard medium, the strain only reached a biomass of 3.4 g/L (DW). *A. niger* D15[egl] grown on SBH gave a Cel7B protein concentration of 0.41 mg/mL after ten days of fermentation, which is almost four times higher than that of the same strain grown on standard medium. Moreover, it was evident that the SBH also served as an excellent growth medium for the recombinant *A. niger* D15[egl] strain (Table 2). *A. niger* D15 [pGT] grown on SBH only reached a biomass of 6.8 g/L (DW). As a comparison, when the *A. niger* D15[pGT] strain used was grown on standard medium, the strain only reached a biomass of approximately 4.1 g/L (DW). Furthermore, fermentation with *A. niger* D15[egl] in SBH resulted in increasing endoglucanase activity for ten days and the highest activity monitored was 2100 nkat/mL (FIG. 3) whereas *A. niger* D15[pGT], lacking the gene for producing endoglucanase, did not give rise to any endoglucanase activity if grown on SBH.

This experiment showed that *A. niger* both have the ability to detoxify the spent bagasse hydrolysate and to grow extremely well in the hydrolysate environment, reaching an even higher biomass production compared to when grown on standard medium. Moreover, a high enzyme amount and high enzyme activity were found when using the recombinant *A. niger* strain able to produce endoglucanase. The amount of enzymes produced was even higher than when grown on standard medium. Consequently, this example demonstrated that the filamentous fungus *A. niger* is suitable for being used as a detoxification biocatalyst when producing ethanol, since it could both detoxify spent hydrolysate and simultaneously produce enzymes.

TABLE 1

|  | Acetic acid | Phenolic compounds | Furfural | HMF |
|---|---|---|---|---|
| BPH | 0.8 | 1.1 | 0.2 | 0.03 |
| BH | 0.8 | 0.9 | 0.1 | 0.02 |
| BHAFS[a] | 0.9 | 0.9 | <0.01 | 0.02 |
| SBH[b] | 0.9 | 1.0 | <0.01 | 0.02 |
| SBHAFA[c] | 0.0 | 0.7 | 0.0 | 0.0 |

Table 1 shows the concentration of inhibitors (g/L) at different stages of the process of detoxifying spent bagasse hydrolysate. The codes used in Table 1 represent the hydrolysate at the different stages: BPH = Bagasse prehydrolysate, BH = Bagasse hydrolysate, BHAFS = Bagasse hydrolysate after fermentation with *Saccharomyces cerevisiae*, SBH = Spent bagasse hydrolysate, SBHAFA = Spent bagasse hydrolysate after eleven days of fermentation with *A. niger* D15[egl].
[a]The hydrolysate was diluted about 5% compared to BH.
[b]The hydrolysate was concentrated <2% compared to BHAFS.
[c]The hydrolysate was diluted about 4% compared to SBH.
Relative standard deviations of the analyses: acetic acid, <10%; phenolic compounds, <12%; furfural and HMF, <5%.

TABLE 2

| *A. niger* strain and growth medium | Endoglucanase activity (nkat/mL)[a] | Cel7B protein concentration (mg/mL)[b] | Endoglucanase activity/Cel7B protein (nkat/mg) | Biomass (DW g/L)[c] |
|---|---|---|---|---|
| *A. niger* D15[egl] grown on SBH | 2100 ± 130 | 0.41 ± 0.06 | 5100 | 9.8 ± 1.6 |
| *A. niger* D15[pGT] grown on SBH | 0 | ND | — | 6.8 ± 1.1 |
| *A. niger* D15[egl] grown on SM | 480 ± 22 | 0.11 ± 0.02 | 4400 | 3.4 ± 0.3 |
| *A. niger* D15[pGT] grown on SM | 0 | ND | — | 4.1 ± 0.5 |

Table 2 shows the volumetric activity, the Cel7B protein concentration, the specific Cel7b activity and the biomass production for *A. niger* grown on spent bagasse hydrolysate and on standard medium. The codes used in Table 2 represent the following: SBH = Spent bagasse hydrolysate, SM = Standard medium, ND = Not detectable.
[a]The endoglucanase activity is calculated as the mean value of the activity measurements of two separate cultures after ten days of fermentation.
[b]The protein concentration is calculated as the mean value from two supernatants from separate fermentation flasks repeatedly analyzed on four SDS gels after ten days of fermentation.
[c]The biomass is calculated as the mean value of two separate cultures made after eleven days of cultivation.

Example 2

Detoxification of Spent Spruce Hydrolysate Using *Aspergillus niger*

Preparation of Spruce Hydrolysate

A spruce hydrolysate was produced by two-step-dilute-acid hydrolysis, as described in Alriksson et al., 2006 (Alriksson, B., et al. *Appl. Biochem. Biotechnol.* 2006, 129-132, p. 599-611).

Fermentation with *S. cerevisiae*

The fermentation of the spruce hydrolysate was performed as with the bagasse hydrolysate described in Example 1, but the flasks with the spruce hydrolysate were given a yeast inoculum of 9 g/L (DW) due to the higher toxicity of the spruce hydrolysate.

Distillation

Distillation was performed as described for the bagasse hydrolysate in Example 1 to provide spent spruce hydrolysate (SSH), which was collected and stored at 4° C. until further use.

*A. niger* Recombinant Strain

The *A. niger* strain D15[egl] described in Example 1 was used for detoxification of spent spruce hydrolysate Detoxification Experiment with *A. niger* Grown on Spent Spruce Hydrolysate Four 100-mL Erlenmeyer flasks (named A-D) were filled with 48 mL of SSH and the fermentation was performed as described in the fermentation experiment in Example 1. Further, Biomass measurement, Enzyme activity assay and SDS-PAGE analysis as well as the Chemical Analyses were performed as described in Example 1.

Results

The inhibitor content in the spruce hydrolysate, the spruce hydrolysate after fermentation with *S. cerevisiae*, the SSH and the SSH after fermentation with *A. niger* D15[egl] are shown in Table 3. It was evident that essentially all the acetic acid, HMF and about 30% of the phenolic compounds were consumed or converted after nine days of fermentation, as seen in SSHAFA in Table 3. Thus, similar to what was found with the spent bagasse hydrolysate, *A. niger* had a surprisingly high detoxification effect on the spent spruce hydrolysate, removing almost all inhibitors.

The volumetric activity, Cel7B protein concentration, specific Cel7b activity and biomass production in the fermentation is presented in Table 4. The SSH reached biomass concentrations of 4.5 g/L (DW), which was higher than when grown on the standard medium. Further, the Cel7B protein concentration was 0.10 mg/mL for the fermentation in SSH, which was similar to the concentration when grown on standard medium, whereas the activity reached 820 nkat/mL, which was higher compared to when grown on standard medium.

Similar to what was found in Example 1, this experiment clearly showed that *A. niger* has the ability to detoxify spent spruce hydrolysate and to grow extremely well in the hydrolysate environment. An even higher biomass production was found when *A. niger* was grown on spent spruce hydrolysate compared to when grown on standard medium. Moreover, a high enzyme amount and high enzyme activity were found when using the recombinant *A. niger* strain able to produce endoglucanase. Consequently, this example demonstrated that the filamentous fungus *A. niger* is suitable for being used as a detoxification biocatalyst when producing ethanol.

TABLE 3

|  | Acetic acid | Phenolic compounds | Furfural | HMF |
|---|---|---|---|---|
| SH | 2.8 | 2.8 | 0.7 | 2.2 |
| SHAFS[a] | 3.0 | 2.8 | 0.0 | 0.9 |
| SSH[b] | 3.0 | 2.9 | 0.0 | 0.8 |
| SSHAFA[c] | 0.1 | 2.0 | 0.0 | 0.04 |

Table 3 shows the concentrations inhibitors (g/L) at different stages of the process of detoxifying spent spruce hydrolysate. The codes used in Table 3 represent the hydrolysate at the different stages: SH = Spruce hydrolysate, SHAFS = Spruce hydrolysate after fermentation with *Saccharomyces cerevisiae*, SSH = Spent spruce hydrolysate, SSHAFA = Spent spruce hydrolysate after nine days of fermentation with *A. niger* D15[egl].
[a]The hydrolysate was diluted about 5% compared to SH.
[b]The hydrolysate was concentrated <2% compared to SHAFS.
[c]The hydrolysate was diluted about 4% compared to SSH.
Relative standard deviations of the analyses: acetic acid, <10%; phenolic compounds, <12%; furfural and HMF, <5%.

TABLE 4

| A. niger strain and growth medium | Endoglucanase activity (nkat/mL)[a] | Cel7B protein concentration (mg/mL)[b] | Endoglucanase activity/Cel7B protein (nkat/mg) | Biomass (DW g/L)[c] |
|---|---|---|---|---|
| A. niger D15[egl] grown on SSH | 820 ± 51 | 0.10 ± 0.01 | 7500 | 4.5 ± 0.0 |
| A. niger D15[egl] grown on SM | 550 ± 52 | 0.11 ± 0.00 | 5000 | 3.2 ± 0.1 |

Table 4 shows the volumetric activity, the Cel7B protein concentration, the specific Cel7b activity and the biomass production for A. niger grown on spent spruce hydrolysate and on standard medium. The codes used in Table 4 represent the following: SSH = Spent spruce hydrolysate, SM = Standard medium, ND = Not detectable.
[a]The endoglucanase activity is calculated as the mean value of the activity measurements of two separate cultures after nine days of fermentation.
[b]The protein concentration is calculated as the mean value from two supernatants from separate fermentation flasks repeatedly analyzed on four SDS gels after nine days of fermentation.
[c]The biomass is calculated as the mean value of two separate cultures made after ten days of cultivation.

Example 3

Removal of Inhibitors from Standard Medium Using *Aspergillus niger*

Fermentation Experiment with *A. niger* Cultivated on Standard Medium with Inhibitors.

An additional experiment was designed to study *A. niger* D15[egl] metabolism of non-sugar compounds in lignocellulose hydrolysates. Eighteen 100-mL Erlenmeyer flasks were filled with 48 mL of standard medium, 1 mL of inhibitor solution, and 1 mL of spore inoculum (or 1 mL of sterile $H_2O$ for control flasks). The flasks were divided into six groups (three flasks per group). Each group had an addition of a different inhibitor solution. Typical compounds found in lignocellulose hydrolysates representing the three main inhibitor categories aliphatic acids, furanaldehydes and phenolic compounds were chosen for the experiment. Group 1 (flasks 1A-C), had an addition of 5 g/L of acetic acid, group 2 (flasks 2A-C) had an addition of 1 g/L of furfural, group 3 (flasks 3A-C) had an addition of 2 g/L of 5-hydroxymethyl-furfural (HMF), group 4 (flasks 4A-C) had an addition of 0.5 g/L of vanillin, group 5 (flasks 5A-C) had an addition of 0.2 g/L of coniferyl aldehyde, and group 6 (flasks 6A-C), had no inhibitor added, but 1 mL sterile $H_2O$ as a volume equalizer. The pH of all flasks was adjusted to 6.3 with NaOH. All the A- and B-flasks were inoculated with *A. niger* D15[egl] ($1 \times 10^6$ spores/mL medium) while the C-flasks (i.e. control flasks) were used to investigate if the concentrations of the inhibitors were affected in absence of *A. niger* cells (for example by degradation or evaporation). All 18 flasks were incubated for nine days in an incubator with shaking at 150 rpm and 30° C. The endoglucanase activity was monitored during the experiment and the biomass was measured at the end of the cultivation as described in Examples 1 and 2. Further, the chemical analyses were performed as described in Examples 1 and 2. The vanillin and coniferyl aldehyde concentrations were measured with HPLC. The XTerra MS $C_{18}$ column was used in the Shimadzu VP series system with UV detection at 254 nm. Elution was performed at a flow rate of 0.4 mL/min with a gradient made of Milli-Q water and acetonitrile, both of which contained 3 mM formic acid. The gradient design consisted of four steps with a total time of 40 min: (i) 25% acetonitrile was applied for 6 min, (ii) the concentration of acetonitrile was increased linearly to 85% during 4 min, (iii) 85% acetonitrile was applied for 12 min, (iv) the concentration of acetonitrile was instantly decreased to 25% and applied for 18 min.

Results

Figure 4:
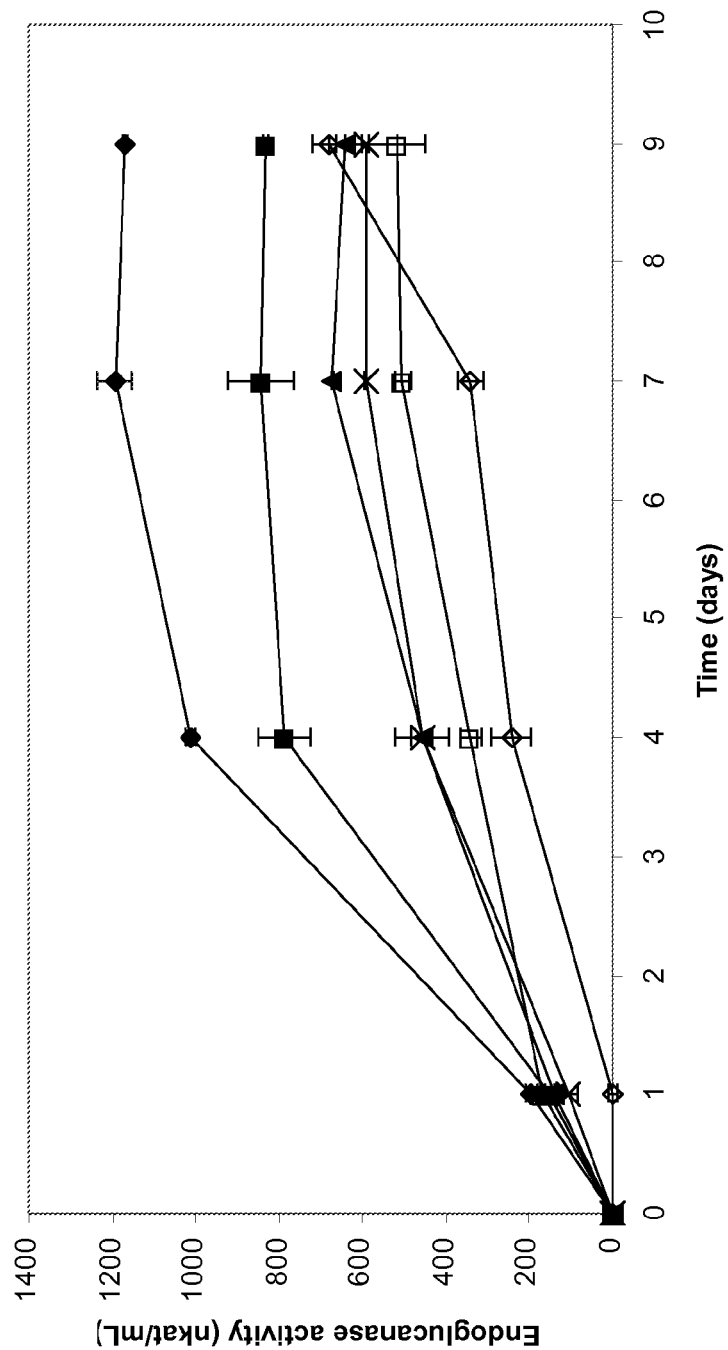
FIG. 4 shows the endoglucanase activity during the removal of inhibitors from standard medium using *A. niger* in Example 3. (♦) *A. niger* D15[egl] grown on standard medium containing 5 g/L acetic acid, (■) *A. niger* D15[egl] grown on standard medium containing 0.5 g/L vanillin, (Δ) *A. niger* D15[egl] grown on standard medium containing 0.2 g/L coniferylaldehyde, (x) *A. niger* D15[egl] grown on standard medium, (□) *A. niger* D15[egl] grown on standard medium containing 2 g/L HMF, (◊) *A. niger* D15[egl] grown on standard medium containing 1 g/L furfural. The endoglucanase activities are calculated as the mean values of the activity measurements of two separate cultures. Error bars indicate the standard deviations.

*A. niger* D15[egl] grew well in all the inhibitor-containing standard media except the one that had an addition of furfural where a lag phase in the growth and enzyme activity was observed (FIG. 4). All the vanillin, acetic acid, coniferyl aldehyde, HMF and furfural were consumed or converted within nine days of fermentation. The fermentation in the medium with an addition of acetic acid showed the highest endoglucanase activity and reached 1200 nkat/mL after seven days whereas the activity of the reference cultivation in the medium without inhibitors reached 590 nkat/mL (day 7) (Table 5). The fermentations with addition of vanillin and coniferyl aldehyde also showed higher or slightly higher enzyme activity than the reference while the HMF and furfural-containing fermentations exhibited lower enzyme activity throughout most of the fermentation experiment. Fermentation in the presence of acetic acid showed the highest specific activity and reached 12,000 nkat/mg, which is about twice as high as that of the reference fermentation and about four times higher than that of the fermentation in presence of furfural. The highest biomass concentration was observed for the cultivation where HMF was added (5.2 g/L (DW)) while the cultivation with added acetic acid had the lowest biomass formation (2.9 g/L (DW)). The reference fermentation had a biomass of 4.4 g/L (DW). The Cel7B protein production was in the range of 0.10-0.15 mg/mL for all fermentations.

Hence, this experiment further demonstrated the unexpected ability of *A. niger* to utilize common inhibitory substances found in hydrolysates for growth. This experiment also demonstrated that *A. niger* is capable of producing enzymes in high concentrations and of high activity when grown in media comprising inhibitory substances, making *A. niger* suitable as a detoxification biocatalyst, e.g. when producing ethanol.

TABLE 5

| A. niger strain and growth medium | Endoglucanase activity (nkat/mL)[a] | Cel7B protein concentration (mg/mL)[b] | Endoglucanase activity/Cel7B protein (nkat/mg) | Biomass (DW g/L)[c] |
|---|---|---|---|---|
| A. niger D15[egl] grown on SM | 550 ± 52 | 0.11 ± 0.00 | 5000 | 3.2 ± 0.1 |
| A. niger D15[egl] grown on SM + acetic acid | 1200 ± 43 | 0.10 ± 0.01 | 12000 | 2.9 ± 0.4 |
| A. niger D15[egl] grown on SM + furfural | 340 ± 33 | 0.12 ± 0.00 | 2800 | 3.5 ± 0.0 |
| A. niger D15[egl] grown on SM + HMF | 500 ± 20 | 0.11 ± 0.00 | 4500 | 5.2 ± 0.3 |
| A. niger D15[egl] grown on SM + vanillin | 840 ± 79 | 0.15 ± 0.00 | 5600 | 4.0 ± 0.1 |
| A. niger D15[egl] grown on SM + coniferyl aldehyde | 670 ± 2 | 0.13 ± 0.00 | 5200 | 4.1 ± 0.1 |

TABLE 5-continued

| A. niger strain and growth medium | Endoglucanase activity (nkat/mL)[a] | Cel7B protein concentration (mg/mL)[b] | Endoglucanase activity/Cel7B protein (nkat/mg) | Biomass (DW g/L)[c] |
|---|---|---|---|---|
| A. niger D15[egl] grown on SM | 590 ± 4 | 0.11 ± 0.01 | 5400 | 4.4 ± 0.3 |

Table 5 shows the volumetric activity, the Cel7B protein concentration, the specific Cel7b activity and the biomass production for *A. niger* D15[egl] grown on standard medium comprising different inhibitors. Results are displayed. The codes used in Table 5 represent the following: SM = Standard medium, HMF = 5-hydroxymethylfurfural.
[a]The endoglucanase activity is calculated as the mean value of the activity measurements of two separate cultures after seven days of fermentation.
[b]The protein concentration is calculated as the mean value from two supernatants from separate fermentation flasks repeatedly analyzed on four SDS gels after seven days of fermentation.
[c]The biomass is calculated as the mean value of two separate cultures made after nine days of cultivation.

Example 4

Recirculation of Process Water After Detoxification of Spent Hydrolysate Using *Aspergillus niger*

Spent hydrolysate from bagasse and spruce is prepared as demonstrated in Example 1 and Example 2. Detoxification is performed by subjecting the spent hydrolysate to a wild type strain of *A. niger*, under conditions described in Example 1 and 2. After 11 days of incubation with *A. niger*, the detoxified hydrolysate is filtered so that biomass of *A. niger* is separated from the detoxified hydrolysate. The purified process water is then recirculated in further processes when preparing spent bagasse and spruce hydrolysate. As an example, a part of the purified process water is mixed with fresh water and used for diluting sulfuric acid used in the pretreatment of sugarcane bagasse as described in Example 1, another part of the purified process water is mixed with fresh water and used to prepare the NaOH solution used in the hydrolysis of sugarcane bagasse as described in Example 1 or used in the two-step-dilute-acid hydrolysis when preparing spruce hydrolysate as described in Example 2, and yet another part of the process water is mixed with fresh water and used to prepare the nutrient solution used in the fermentation of bagasse or spruce hydrolysate with *S. cerevisiae* described in Example 1. This process is schematically illustrated in FIG. 1.

Example 5

Recirculation of Process Water and Produced Saccharification Enzymes After Detoxification of Spent Hydrolysate Using *Aspergillus niger*

Figure 2:
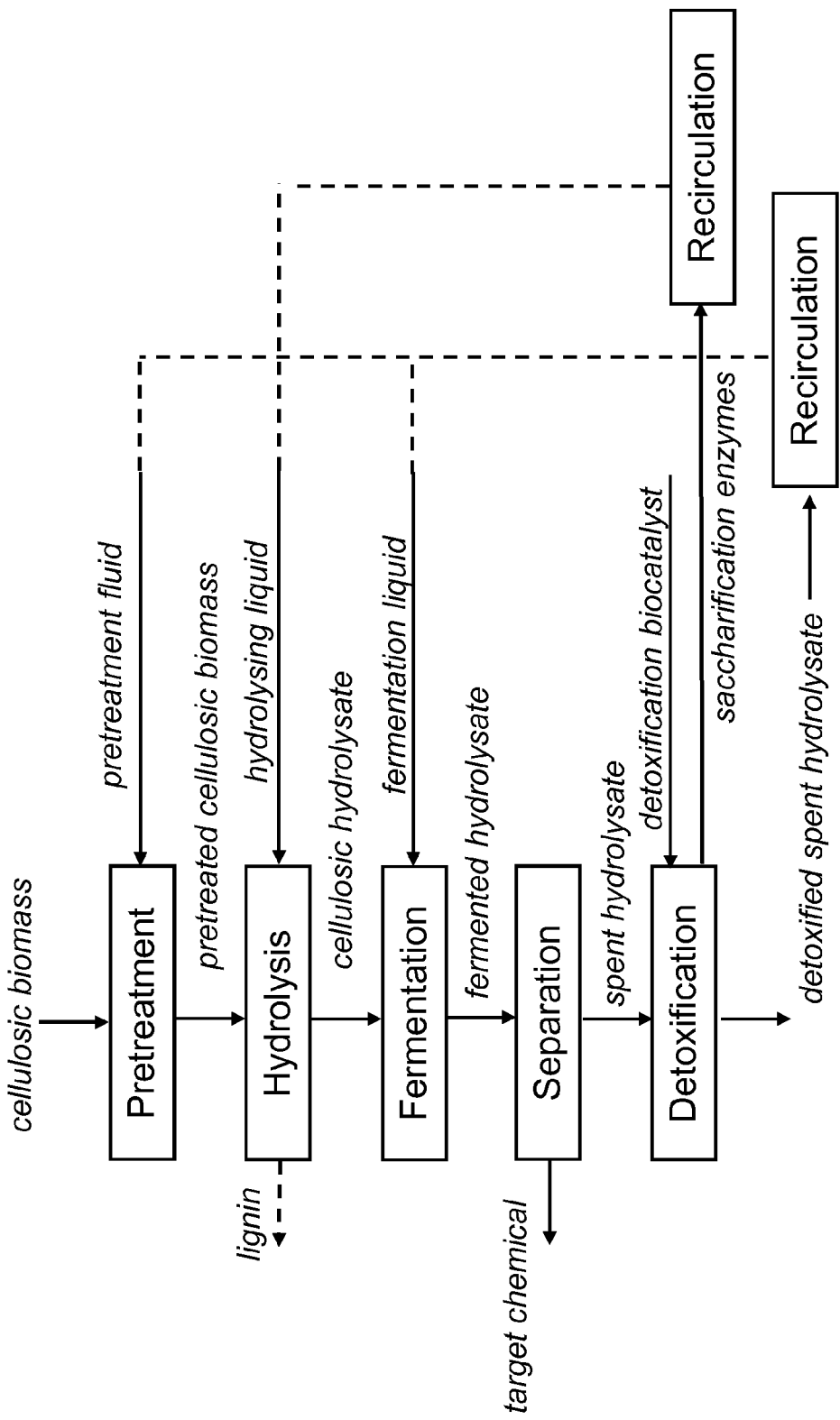
FIG. 2 shows an embodiment of the disclosed method for producing a target chemical from cellulosic biomass, wherein produced saccharification enzymes are recirculated.

Spent hydrolysate from bagasse and spruce is prepared as demonstrated in Example 1 and Example 2. Detoxification is performed by subjecting the spent hydrolysate to a recombinant *A. niger* strain expressing a saccharification enzyme under conditions described in Example 1 and 2. The purified process water is recirculated in further processes when preparing spent bagasse hydrolysate and spruce as described in Example 4. The produced saccharification enzymes are concentrated and then stored for later use, or added in further hydrolysis of bagasse prehydrolysate. As an example, the produced saccharification enzymes are mixed with the cellulases and cellobiases described in Example 1 above, and added to the bagasse or spruce prehydrolysate. This process is schematically illustrated in FIG. 2.

The invention claimed is:
1. A method for preparing at least one target chemical obtained from cellulosic biomass involving detoxification of spent hydrolysate, comprising the steps of:
 a) providing cellulosic biomass;
 b) subjecting the cellulosic biomass to at least one aqueous pretreatment fluid to provide pretreated cellulosic biomass;
 c) subjecting the pretreated cellulosic biomass to at least one aqueous hydrolysing liquid, optionally comprising saccharification enzymes, under conditions in which at least a part of the pretreated cellulosic biomass is hydrolysed to a cellulosic hydrolysate, said cellulosic hydrolysate comprising fermentable sugars and inhibitory substances;
 d) subjecting the fermentable sugars to fermentation in an aqueous liquid utilizing at least one fermentation biocatalyst under conditions in which at least a part of the fermentable sugars are fermented into a primary target chemical;
 e) separating the primary target chemical from the fermented hydrolysate to provide a spent hydrolysate comprising inhibitory substances;
 f) detoxifying the spent hydrolysate by decreasing the concentration of at least one of the inhibitory substances using a detoxification biocatalyst selected from the group consisting of wild type, mutant and recombinant filamentous fungi, to provide a detoxified spent hydrolysate;
 g) recirculating at least a part of the detoxified spent hydrolysate, optionally after further purification, as a part of aqueous liquid(s) provided in at least one of steps b), c) and d).

2. The method according to claim 1, wherein the fermentation biocatalyst of step d) is yeast, and the primary target chemical of step d) is ethanol.

3. The method according to claim 2, wherein the fermentation biocatalyst is wild type, mutant or recombinant *Saccharomyces cerevisiae*.

4. The method according to claim 1, wherein the cellulosic biomass of step a) is selected from wood material, municipal paper waste, agricultural residues, such as bagasse, and energy crops.

5. The method according to claim 1, wherein the aqueous pretreatment liquid of step b) has a pH of below 5.

6. The method according to claim 1, wherein the detoxification biocatalyst of step f) is a fungus selected from wild type, mutant or recombinant *Aspergillus, Trichoderma, Rhizopus, Mucor*, or a combination thereof.

7. The method according to claim 6, wherein the detoxification biocatalyst is wild type, mutant or recombinant *Aspergillus niger* or *Hypocrea jecorina*.

8. The method according to claim 1, wherein the detoxification biocatalyst produces enzymes during the detoxification in step f).

9. The method according to claim 8, wherein the enzymes are saccharification enzymes.

10. The method according to claim 9, wherein the saccharification enzymes obtained in step f) are added in the aqueous hydrolysing liquid in step c).

11. The method according to claim 1, wherein the inhibitory substances comprise furans, aliphatic acids and/or phenolic compounds.

12. A system for producing at least one target chemical obtained from cellulosic biomass, comprising;

a) at least one cellulosic biomass pretreatment vessel for pretreating at least a part of provided cellulosic biomass to pretreated cellulosic biomass, connected to b) a hydrolysis vessel for hydrolysing at least a part of the pretreated cellulosic biomass to cellulosic hydrolysate, said cellulosic hydrolysate comprising fermentable sugars and inhibitory substances, further connected to c) a fermentation vessel comprising a fermentation biocatalyst for fermenting at least a part of the fermentable sugars, providing a fermented hydrolysate comprising a primary target chemical and inhibitory substances, further connected to d) a first separation means, for separating the primary target chemical from the fermented hydrolysate and for providing a spent hydrolysate, further connected to e) a detoxification vessel, comprising a detoxification biocatalyst selected from the group consisting of wild type, mutant and recombinant filamentous fungi, for detoxifying the spent hydrolysate from at least one inhibitory substance and for providing a detoxified spent hydrolysate, further connected to f) recirculation means for recirculating at least a part of the detoxified spent hydrolysate to at least one of the following pretreatment vessel of a), the hydrolysis vessel of b) and the fermentation vessel of c), wherein the hydrolysis vessel and the fermentation vessel may be the same vessel or two different vessels.

13. System according to claim 12, wherein the detoxification vessel of e) is connected to the recirculation means f) via second separating means for separating detoxification biocatalyst from at least part of the detoxified spent hydrolysate.

14. Method of detoxifying spent lignocellulosic hydrolysate comprising contacting the spent lignocellulosic hydrolysate with a wild type, mutant or recombinant filamentous fungi.

15. Method according to claim 14, wherein the filamentous fungi is wild type, mutant or recombinant *Aspergillus niger* or *Hypocrea jecorina*.

16. Method according to claim 14, wherein the detoxification involves removal of at least one inhibitory substance selected form the group consisting of furans, aliphatic acids and phenolic compounds.

* * * * *